United States Patent [19]

Hill et al.

[11] 4,301,414

[45] Nov. 17, 1981

[54] DISPOSABLE SAMPLE CARD AND METHOD OF MAKING SAME

[75] Inventors: Jeremy R. Hill, Weston; Allen E. Meyer, Greenwich, both of Conn.

[73] Assignee: United States Surgical Corporation, Norwalk, Conn.

[21] Appl. No.: 89,088

[22] Filed: Oct. 29, 1979

[51] Int. Cl.³ .......................................... G01R 27/22
[52] U.S. Cl. ................................ 324/446; 29/592 R; 29/876
[58] Field of Search ............... 324/446, 441, 442, 447, 324/448, 450, 65 R, 64; 29/592 R, 876, 877; 128/637, 669; 73/344, 343.5

[56] References Cited

U.S. PATENT DOCUMENTS

| Re. 30,007 | 5/1979 | Steuer et al. | |
|---|---|---|---|
| 3,699,437 | 10/1972 | Ur | 324/65 R |
| 3,781,659 | 12/1973 | Ur | |
| 3,896,373 | 7/1975 | Zelby | 324/65 R X |
| 3,922,598 | 11/1975 | Steuer et al. | 324/442 |
| 4,123,701 | 10/1978 | Josefsen et al. | 324/448 |

OTHER PUBLICATIONS

Changes in the Electrical Impedance of Blood during Coagulation, Nature, vol. 226, Apr. 18, 1970, pp. 289 & 270.

*Primary Examiner*—Stanley T. Krawczewicz
*Attorney, Agent, or Firm*—Fleit & Jacobson

[57] ABSTRACT

A disposable sample for use in measuring a parameter of a liquid sample such as the hematocrit and a method of making same. The disposable sample card is a microvolume conductivity cell precision molded from plastic with built-in stainless steel electrodes. The sample card comprises a planar base portion on which is defined a capillary tube. First and second electrodes are disposed within the capillary tube in a spaced relationship and define a volume within the capillary tube. This volume constitutes a conductivity cell. The sample card may be used with an instrument which basically comprises an electronic portion for processing data obtained from the liquid sample on the sample card, a front-end mechanism for positioning the sample card within the instrument, and a digital display for displaying in eye-readable form the results of a parameter measurement made in the instrument.

38 Claims, 18 Drawing Figures

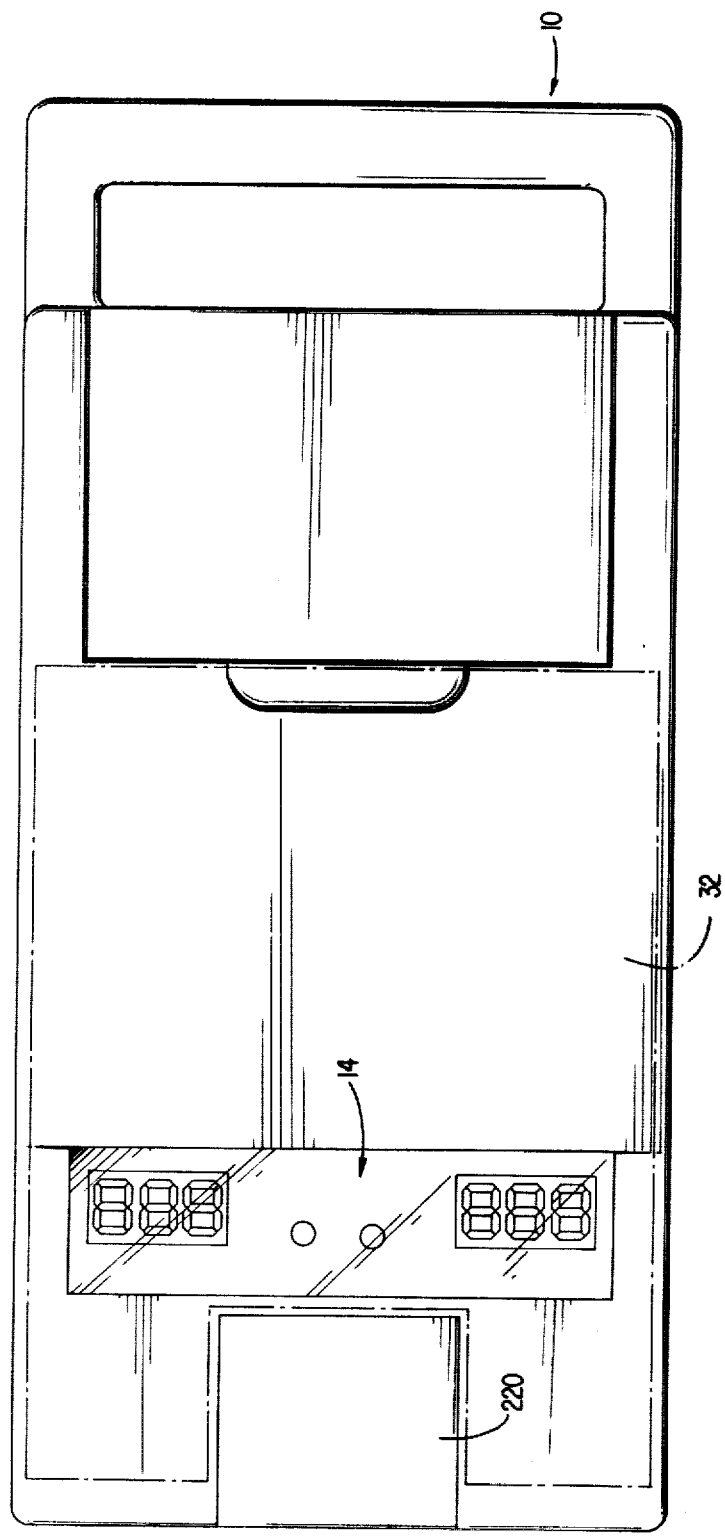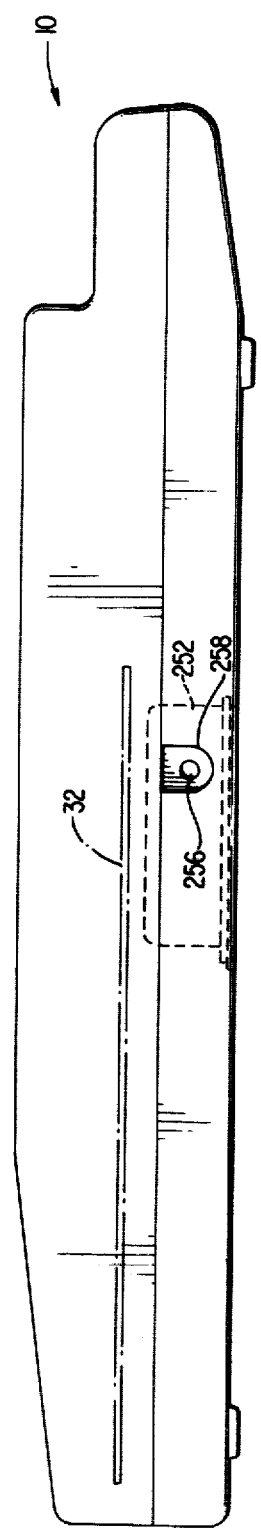

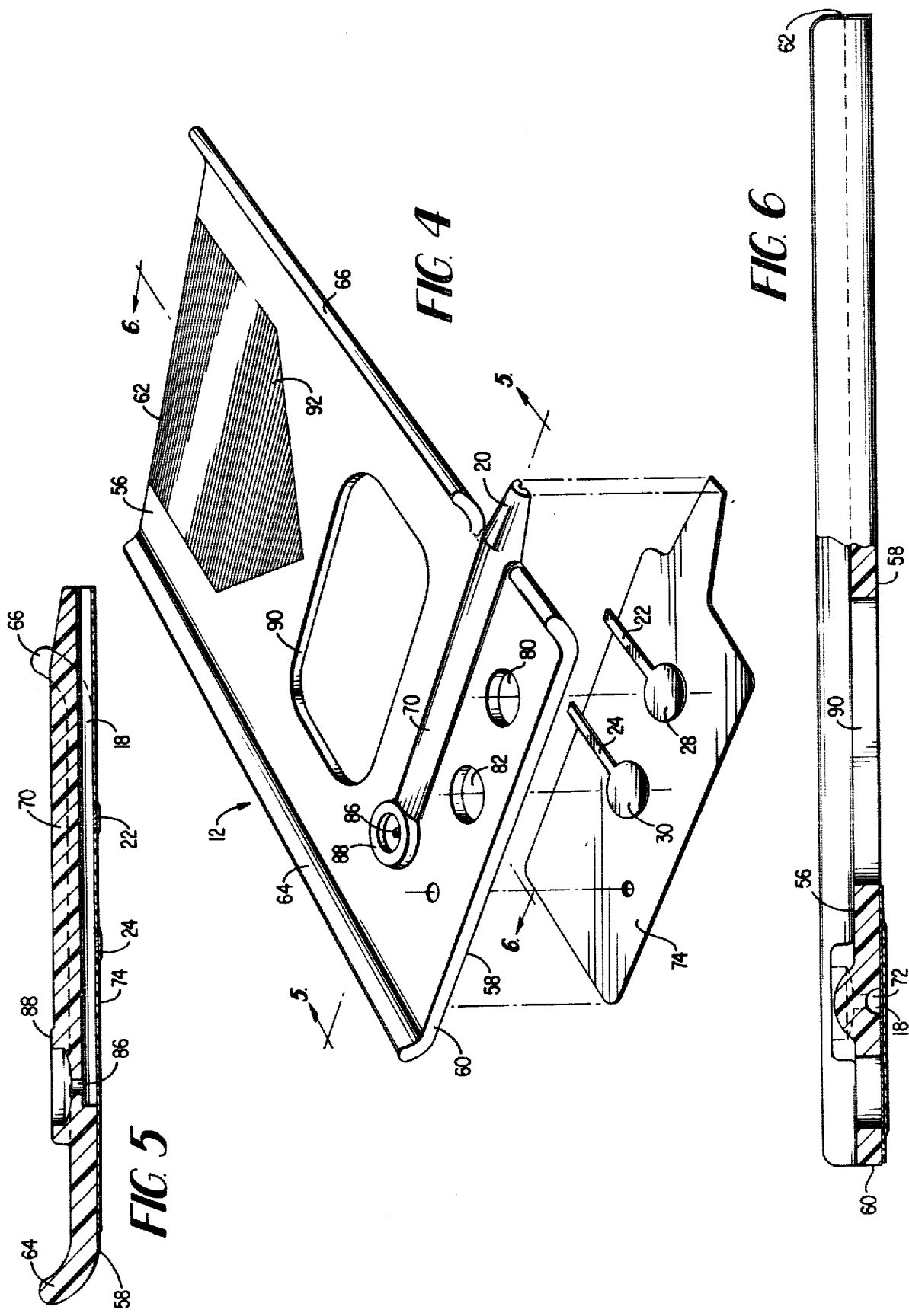

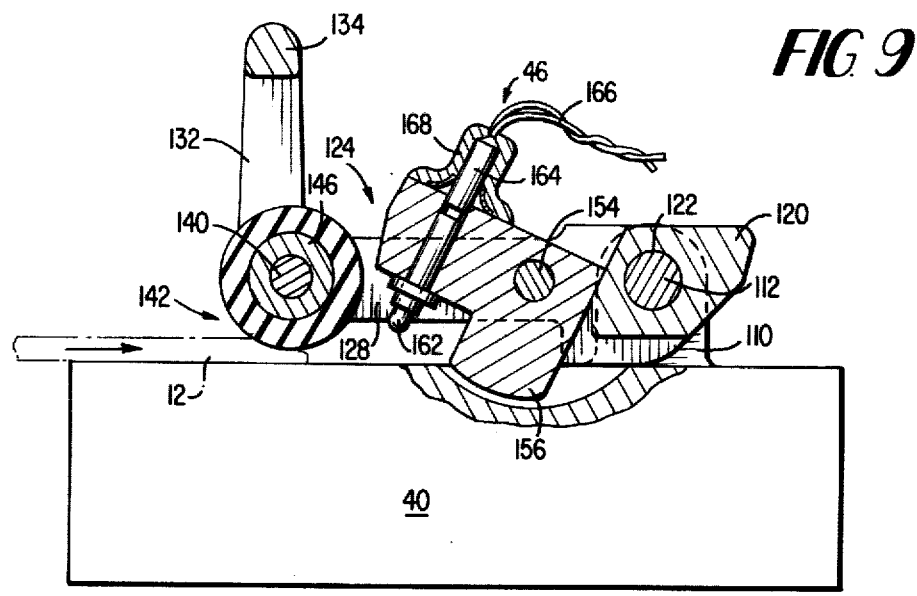
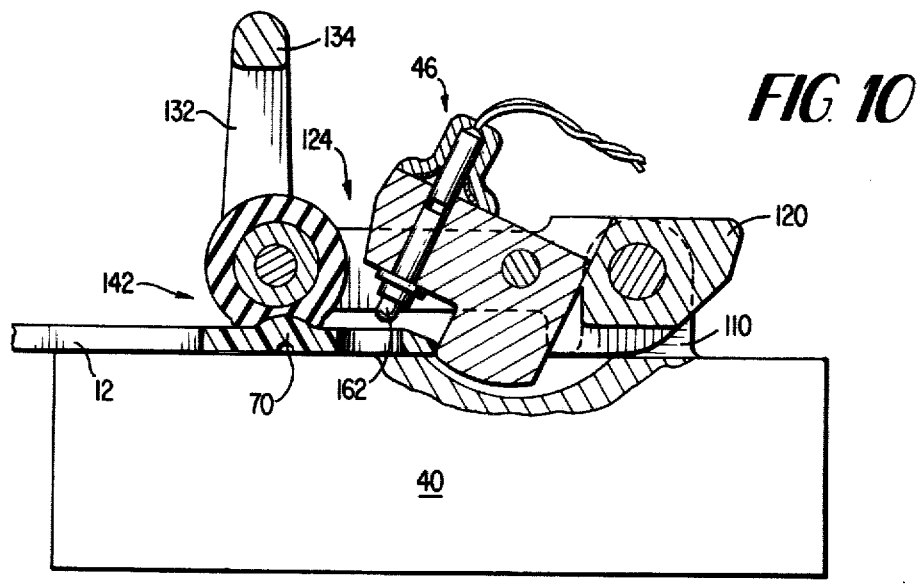

DISPOSABLE SAMPLE CARD AND METHOD OF MAKING SAME

BACKGROUND OF THE INVENTION

1. Field of the Invention

This invention relates to liquid sample testing, in general, and to a liquid sample carrier and method of making same, in particular.

2. Background of the Prior Art

Various methods and apparatus are known for studying liquid samples. Some involve centrifugation, others utilize agitation, and there are still others which depend upon the electrical characteristics of the sample being tested. In virtually all of these known techniques, especially those in the medical field, it is of prime importance to maintain isolation between samples. A still further problem relates to the protection of the technician against contracting infectious diseases from the samples under test. With the known methods and apparatus, very little protection is afforded.

An example of an apparatus for studying the electrical characteristics of blood can be found in U.S. Reissue Pat. No. Re. 30,007, issued to Steuer et al. on May 22, 1979. This apparatus includes a rod-like probe having two conductive electrodes at the tip of the probe. A blood sample is associated with the electrodes of the probe, and an electrical current is applied across the blood for the purpose of hematocrit determinations. Obviously, the probe must be thoroughly cleaned between tests to ensure accurate test results.

An example of disposable blood sample card is shown in U.S. Pat. No. 4,123,701, filed on July 1, 1976, to inventors Josefson and Veth, and assigned to United States Surgical Corporation. The blood sample card described therein is a disposable blood sample carrier comprising a substantially planar base portion made of an electrically insulating material. The card is sterilized, pre-packaged and disposable after a single use. In the base portion of the card is a well to receive the blood sample. The well is sized so as to accommodate approximately one drop of blood, and a well volume on the order of 0.05 ml is described. Electrodes are positioned in the well and are adapted to be connected to an instrument that evaluates the electrical characteristics of the blood sample by means of electrical circuitry, as disclosed, for example, in the aforementioned U.S. Reissue Patent No. Re 30,007.

The measuring instrument and blood sample card just described, are considered to be exemplary of the present state of the art. Nevertheless, there is a need for a disposable liquid sample carrier which provides a simplified, safe and accurate electrical evaluation of liquid samples. The present invention is directed toward filling that need.

SUMMARY OF THE INVENTION

The present invention generally relates to testing of liquid samples by electrical means. Particularly, use is found for the invention in the medical field, especially in studying the electrical conductivity of whole blood samples and the like.

Specifically, subject invention comprises a disposable blood sample card or carrier for use with an instrument, which is a hand-held, battery-operated device used for the fast and simple measurement of blood conductivity, such as hematocrit. The instrument accepts the disposable sample card, which is used for the one time conveyance and application of a liquid sample, such as blood, to the instrument.

The instrument has provision for digital displays for read-outs of hematocrit and the approximate equivalent of hemoglobin. There are no external switches on the instrument, and power is automatically applied when the disposable sample card is inserted into the instrument.

The measurement technique employed by the system is based on the well-known conductivity principle. Briefly, this principle states that blood serum acts as a conductor, while the red blood cells act as insulators. If an alternating current is passed through a whole blood sample of well defined volume and temperature, its conductivity will be inversely related to the number of red blood cells per unit volume. Therefore, if the conductivity of the blood sample is known, the hematocrit can be determined.

Blood serum also exhibits a rather extreme temperature coefficient which directly affects blood conductivity. Therefore, the system of the present invention also measures the temperature of the blood sample and, using this data together with the conductivity measurement, calculates the hematocrit value. An approximation of hemoglobin is also provided. In the present system, hemoglobin is determined by dividing the hematocrit value by 3.

In a preferred embodiment, the blood sample card is a micro-volume conductivity cell precision molded from plastic with built-in stainless steel alloy electrodes. Basically, the sample card comprises a planar base portion on which is defined a capillary tube. A nozzle located at the end of the capillary tube provides an entrance for a blood sample to enter the capillary tube. First and second electrodes are disposed within the capillary tube in a spaced relationship and define a volume within the capillary tube. This volume, defined between the two electrodes within the capillary tube constitutes the conductivity cell.

Each of the electrodes is electrically connected to a conductive pad that provides a means for associating the blood sample with the electronics contained in the instrument to make a conductivity measurement of the sample.

The instrument, in accordance with the teachings of the subject invention, basically comprises an electronic portion for processing data obtained from the blood sample on the sample card, a front end mechanism for positioning the blood sample card within the instrument, and a digital display for displaying in eye-readable form the results of a hematocrit measurement made in the instrument.

The front end mechanism of the instrument contains an indexing member associated with a block or base portion so that proper insertion of the sample card within the instrument is assured. The base portion is preferably made of a material exhibiting excellent heat-conducting characteristics. One such material is aluminum.

A roller assembly within the instrument holds the sample card in intimate contact with the top surface of the base portion. Also provided as part of the front end mechanism is a generally L-shaped bracket which contains electrical contact assemblies. The L-shaped bracket is pivotally mounted in the mechanism so that, upon insertion of the sample card, the contact assemblies are brought into electrical association with the pads on the disposable sample card.

The distance between the blood sample in the capillary tube and the bottom of the disposable sample card is kept to a minimum through the use of very thin sheet of plastic material, such as Mylar. This is done so that, when the sample card is positioned within the instrument, the blood sample is in close contact with the base portion of the front end mechanism. In this way, the blood sample, after a very short period of time, assumes the temperature of the base portion. A thermistor is imbeded in the base of the front end mechanism near where the blood sample will be located when the sample card is inserted into the instrument. In this way, data relating to the temperature of the base portion, which is also the temperature of the blood sample, can be presented to the electronic circuitry within the instrument for subsequent processing.

Each of the electrical contact assemblies contains a lead which is presented to the electronic circuitry to accomplish the application of an excitation current across the blood sample and the attendant measurement of the conductivity of the blood sample.

The construction of the disposable sample card produces many observable advantages over similar prior art devices. The disposable sample card readily capillarizes the blood sample and makes it easy for sample collection directly from a patient or from a test tube. The disposable sample card is translucent and the capillary section provides a magnifying area so that any air pockets or other discontinuities in the blood sample are readily apparent. On the top surface of the sample card, the magnifying area of the capillary section provides a bump, which acts as a locator once the disposable sample card is pushed into the front end mechanism of the instrument. The distance between the bottom of the disposable blood sample carrier and the blood sample in the capillary tube is kept to a minimum so that there is excellent heat transfer between the blood sample and the heat-conducting base portion of the front end mechanisn. In addition, the sample card contains a cut-out near the blood sample which acts to decrease the thermal mass in the area of the blood sample, thus, promoting heat transfer between the blood sample and the base portion.

The instrument, associated with the sample card, is powered by a self-contained, rechargeable battery and is completely portable. There are no switches, adjustments or calibrations available to the operator, not even a power switch. Insertion of the disposable sample card turns the power on and removal of the sample card turns the power off.

It is thus a principle object of the present invention to provide a liquid sample carrier for rapid and accurate measuremnt of conductivity of a liquid sample.

It is another object of the present invention to provide a completely portable system employing a disposable sample card for measuring hematocrit within a blood sample taken directly from a patient or from a test tube.

It is still an object of the present invention to provide a disposable sample card for receiving liquid samples and for determining a characteristic of such samples through electrical means.

It is yet an object of the present invention to provide a technique for testing body fluids in a manner which avoids cross-contamination of samples and which minimizes the possibility of its technician contracting a disease.

It is a further object of the present invention to provide a disposable sample card for electrical evaluation of body fluids, such as hematocrit determinations.

It is still another object of the present invention to provide a disposable sample card that is easy to manufacture at a minimum cost.

These and other objects of the present invention, as well as many of the attendant advantages thereof, will become more readily apparent when reference is made to the following description, taken in conjunction with the accompanying drawings.

BRIEF DESCRIPTION OF THE DRAWINGS

FIG. 2 is a top plan view of the instrument shown in FIG. 1 with the front end mechanism cover in place.

FIG. 3 is a side plan view of the instrument shown in FIG. 1.

FIG. 4 is an exploded perspective view showing the elements constituting a preferred embodiment of a disposable sample card.

FIG. 5 is a view taken along lines 5—5 of FIG. 4.

FIG. 6 is a view taken along lines 6—6 of FIG. 4.

FIGS. 9 through 12 are longitudinal sections partially cut away from the front end mechanism shown in FIG. 8.

DETAILED DESCRIPTION OF THE DRAWINGS

Figure 1:
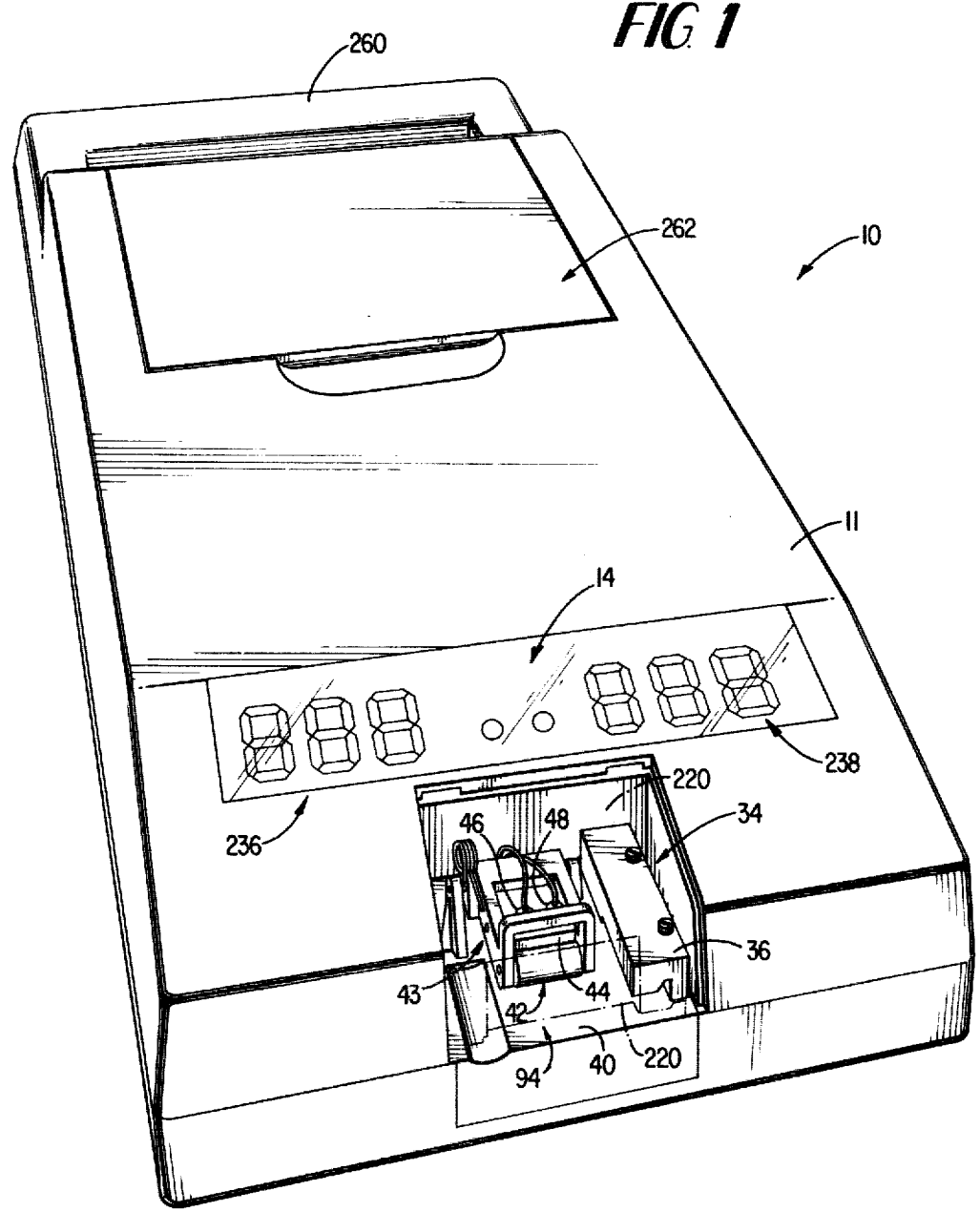
FIG. 1 is a perspective view showing a preferred embodiment for the instrument with the front end mechanism cover in phantom for use in the liquid conductivity measuring system.
Figure 7:
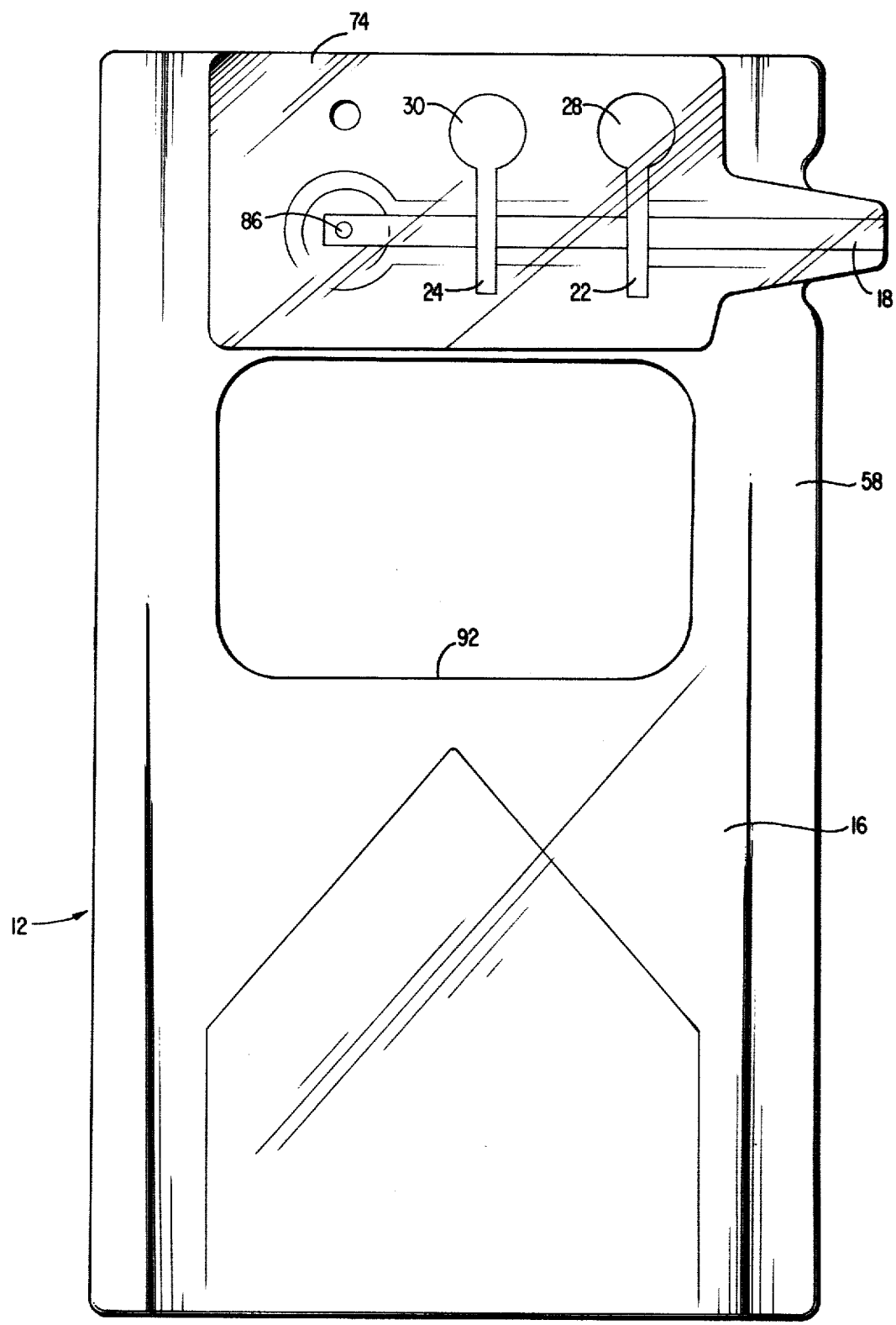
FIG. 7 is bottom plan view of the disposable sample card illustrated in FIG. 4.

The present invention generally relates to testing of liquid samples by electrical means. Particularly, use is found for the invention in the medical field, especially studying the electrical conductivity of whole blood samples and the like.

Specifically, with reference to FIGS. 1-3 and 8, the system, according to the subject invention, comprises an instrument, generally designated as 10, and a disposable blood sample card or carrier, generally designated as 12. The instrument 10 is a hand-held battery operated device used for the fast and simple measurement of blood conductivity, such as hematocrit and an approximation of hemoglobin. The instrument accepts the disposable sample card, which is used for the one-time conveyance and application of a liquid sample, such as blood, to the instrument.

The instrument 10 has provision for digital displays 14 for read-outs of hematocrit and the approximate equivalent of hemoglobin. There are no external switches on the instrument, and power is automatically applied when the disposable sample card 12 is inserted into the instrument.

In a preferred embodiment, the blood sample card, as best seen in FIGS. 4–7, is a micro-volume conductivity or measurement cell precision molded from plastic with built-in stainless steel alloy electrodes. Basically, the sample card 12 comprises a planar base portion 16 on which is defined a capillary tube 18. A nozzle 20 located at the end of the capillary tube, provides an entrance for a blood sample to enter the capillary tube. First and second electrodes 22 and 24 are disposed within the capillary tube in a spaced relationship and define a volume within the capillary tube. This volume, defined between the two electrodes within the capillary tube constitutes the conductivity or measurement cell 26.

Each of the electrodes 22 and 24 is electrically connected to a conductive disc or pad 28 and 30 that provides a means for associating the blood sample with the electronics 32 contained in the instrument to make a conductivity measurement of the liquid sample. One form of electronics which may be used with the disposable sample card is that disclosed in co-pending U.S. Patent Application Ser. No. 089,087, entitled, "Electrical Liquid Conductivity Measuring System," filed on even date herewith in the names of Hill and Meyer, assigned to United States Surgical Corporation, and incorporated by reference herein.

Again with reference to FIGS. 1–3, the instrument basically comprises an electronic portion 32 for processing data obtained from the blood sample on the sample card, a front end mechanism 34 for positioning the blood sample card within the instrument, and a digital display 14 for displaying in eye-readable form, the results of a hematocrit measurement made in the instrument.

The front end mechanism 34 of the instrument 10 contains an indexing member 36 associated with a block or base portion 40 so that proper insertion of the sample card 12 within the instrument is assured. The base portion 40 is preferably made of a material exhibiting excellent heat conducting characteristics. One such material is aluminum.

A roller assembly, generally designated as 42, within the instrument holds or registers the sample card in intimate contact with the top surface of the base portion. Also provided as part of the front end mechanism is a generally L-shaped bracket 44 which contains electrical contact assemblies 46 and 48. The L-shaped bracket is pivotally mounted in the mechanism so that, upon insertion of the sample card, the contact assemblies are brought into electrical association with the pads 28 and 30 on the disposable sample card 12.

Having briefly discussed the liquid conductivity measuring system, a detailed description of the disposable blood sample card and intrument will now be provided.

With reference to FIGS. 4–8, there is shown a preferred embodiment of the disposable blood sample carrier, generally designated as 12, which basically comprises a substantially planar body 16 that defines a capillary tube 18 within which are situated two spaced apart electrodes 22 and 24. The electrodes, typically, are approximately 0.28 inch apart. The portion of the capillary tube 18 located between the electrodes 22 and 24 form a conductivity or measurement cell 26 wherein a blood sample resides during measurement of hematocrit. Associated with each of the electrodes are electrically conductive pads 22 and 24, respectively, which are used to interface the measuremnt cell 26 with the measuring instrument.

Figure 8:
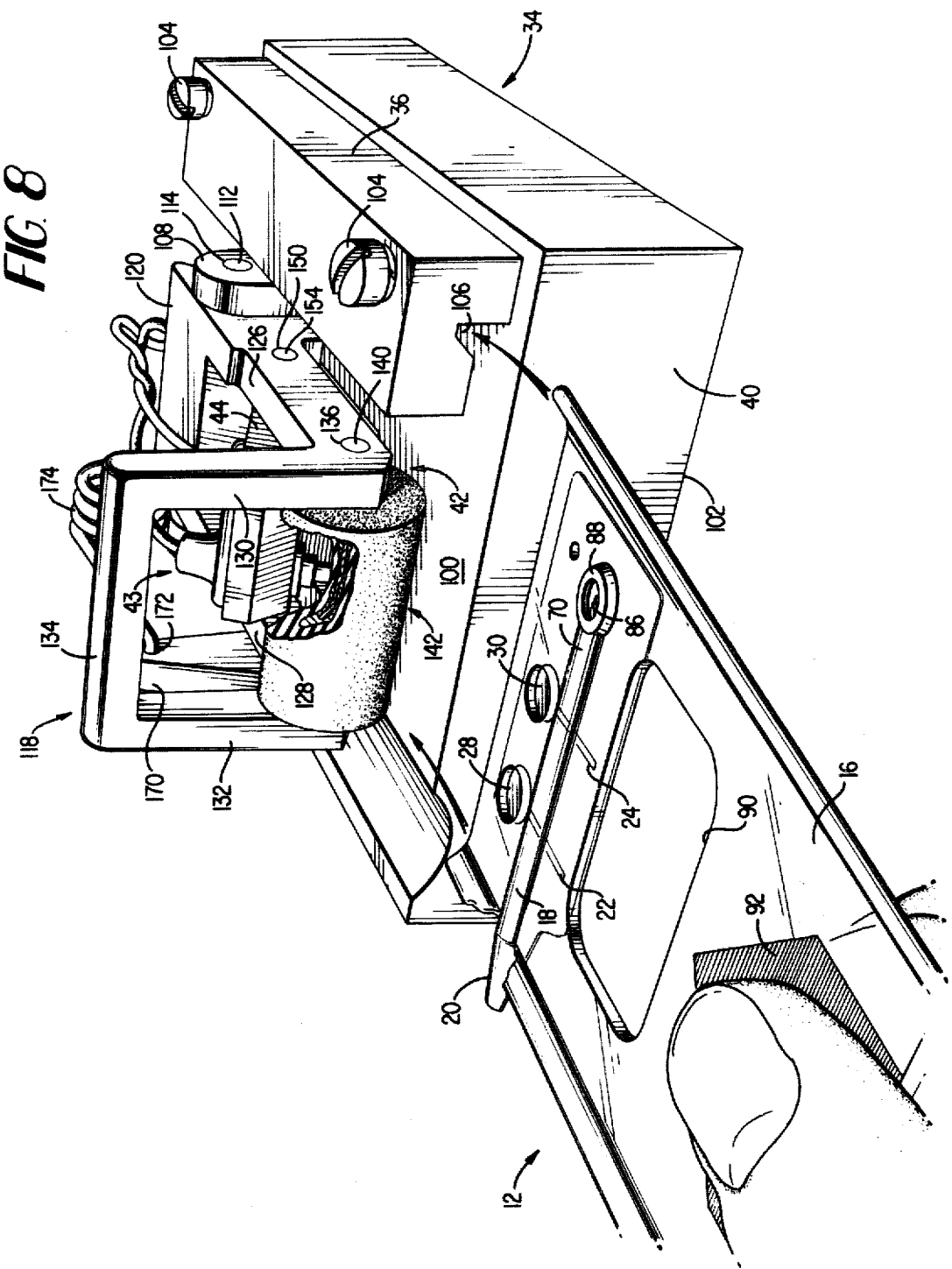
FIG. 8 is a perspective view showing an embodiment for the front end mechanism of the instrument with a sample card about to be inserted.

As best seen in FIGS. 4–7, the sample card 12 comprises an elongated substantially planar body portion 16 typically made from a translucent plastic material. The length of the body portion is typically 2.50 inches whereas the width of the body portion is typically 1.44 inches. With reference to FIG. 8, which shows the blood sample carrier in its position of intended use with respect to the measuring instrument along with FIGS. 4–7, the main body 16 defines a planar top surface 56 and a planar bottom surface 58. The body terminates in a front wall 60 and a rear wall 62. The sides of the body portion, each terminate in a wing portion 64 and 66 out of the plane defined by the top surface 56. When viewed in cross section, each of the wing portions is typically a curved section which deviates from planarity in a smooth and continuous fashion.

Near the front end of the main body portion there is defined a transversely extending raised portion 70, part of which interrupts wing portion 66 as it extends beyond the side wall of the main body. A semi-cylindrical transversely extending groove 72 having a radius approximately 0.03 inch is defined by the raised portion 70 on the bottom surface 58 of the body portion 12.

An overlay 74, typically made from a suitable plastic such as Mylar and having a typical thickness of 0.002 inch, is adhesively secured to the bottom surface 58 of the body portion. The overlay is die-cut so that it completely covers the semi-cylindrical groove and thus defines a capillary tube 18 having a nozzle portion 20 for receiving a blood sample either from the finger of a patient or from a test tube.

Adhesively secured to the overlay and interposed between the overlay and the bottom surface of the body portion are the pair of electrodes 22 and 24. The electrodes are positioned so that they extend transversely within the capillary tube and are spaced apart to define the measurement cell 26. Each of the electrodes terminate in a disc-shaped electrically conductive pad 28, 30 which is used in connection with the measurement instrument 10 in a manner to be described in greater detail hereinafter. The main body portion 16 contains a pair of apertures 80 and 82 which allow the measurement cell 26 to interface with the measuring instrument via the disc pads 28 and 30.

The other end of the capillary tube terminates in a fine aperture 86 having a typical diameter of 0.03 inch which provides a means for evacuating the air within the capillary tube when the blood sample is being drawn into the tube by capillary action. A raised rim 88 completely surrounds the aperture and provides an interface for use with conventional, automatic liquid dispensers used in cleaning, testing and surfactant adding during manufacture of the sample card.

Near the capillary tube, the main body contains a large rectangular cut-out 90 which is used to decrease the thermal mass of the body portion in the area near the blood sample. The typical dimensions of the rectangular cut-out are approximately 1.19 inch by 0.63 inch.

Additional structure and features of the blood sample carrier will be presented hereinafter when discussing the association between the sample card 12 and the instrument 10 used to make an automatic measurement of hematocrit. At this point, however, a discussion of how the disposable sample card is manufactured will now be presented.

The main body portion 12 is manufactured by conventional injection molding techniques and is made from a plastic material which has good wetting properties to facilitate the capillary action taking place within the capillary tube 18. In addition, the plastic material should b translucent. The main body portion may be made from such materials as polycarbonate (LEXAN), polymethyl methacrylate (plexiglas), or some form of styrene-butadiene resin (K-resin).

The overly 74 is made in the following manner. A double sided adhesive sheet has backing paper on both sides to prevent loss of the adhesive quality of the sheet. The backing is removed from one side of the adhesive sheet, and the exposed adhesive surface is placed onto a sheet of Mylar. The backing paper on the other side of the adhesive sheet is now removed and a sheet of stainless steel having a typical thickness of 0.005 inch is bonded to the exposed adhesive surface. The stainless steel may be passivated prior to being secured to the Mylar sheet. The result is a laminant consisting of stainless steel bonded to Mylar.

A conventional etching technique is employed to remove the stainless steel from the Mylar sheet in all places except those where the electrodes 22, 24 and disc pads 28, 30 are formed. The areas of the stainless steel denoting the electrodes and the disc pads are coated with a photo-resist such as the type commonly used in the production of electronic printed circuit boards. The stainless steel with photo-resist is exposed to light and then an etchant, such as feric chloride is applied. The etchant is of such a type that it does not attack the adhesive. The result is two electrodes 22, 24 with associated disc pads 28, 30 etched onto the Mylar overlay 74 with sticky surface everywhere except where the stainless steel is. The backing paper is then replaced over the etched overlay and the overlay is die-cut into the shape shown in FIG. 3.

It is also contemplated that the etching technique may be eliminated and an alternative method may be employed to secure the electrodes to the overlay. A stainless steel ribbon may be presented directly across the overlay and die cut as it is secured to the adhesive of the overlay.

The main body portion 16 is bonded to the overlay 74 by removing the backing paper from the overlay and pressing the two together, employing a conventional rolling technique. The positioning of the Mylar on the under surface 58 of the body part 16 is not critical as long as the capillary tube 18 is correctly formed and the two stainless steel electrodes 22, 24 traverse the capillary tube at substantially right angles.

With reference to FIGS. 8-17, the details of the mechanical front end mechanism 34 of the instrument 10 will now be described. The front end mechanism receives the sample card 12 in order to initiate measurement of hematocrit in the instrument. FIG. 8 shows the mechanism 34 in the position of intended use with the instrument housing 11 removed.

The front end mechanism 34 basically comprises a base portion 40 to which is attached an indexing block 36 for positioning the sample card when it is inserted into the instrument. Pivotally mounted to the reference block is a tension roller assembly 42 and an electrical contact assembly 43.

Basically, a disposable sample card 12 loaded with a blood sample is held with the molded indicating arrow 92 up and pointed toward the instrument and, then, inserted into the opening 94 provided on the facing edge of the instrument. The two contact assemblies 46 and 48 of the mechanism 34 make electrical contact with pads 28 and 30 of the sample card 12. The electronics portion 32 of the instrument probes the sample card, measures the front end block temperature, measures the conductivity of the blood sample, computes the hematocrit percentage and displays it on a digital display 14.

As shown in its position of intended use in FIG. 8, the front end mechanism 34 contains a base portion or reference block 40 which may take the form of a regular six-sided solid. The block defines a top surface 100 on which the sample card rides preparatory to positioning within the front end mechanism. The block also defines a bottom surface 102 by means of which the mechanism is mounted within the housing 11 of the instrument 10 by a suitable fastening means such as screws (not shown). The block is preferably made of a material which exhibits excellent heat conduction characteristics. One such material is aluminum.

Attached to the top surface of the block 40 is an elongated indexing member 36 which is fixed to the block by a suitable fastening means such as the screws 104. A groove 106 which mates with the wing portion 64 of the sample card extends along the length of the indexing member 36 a sufficient distance to permit the proper indexing of the sample card within the instrument.

Figure 13:
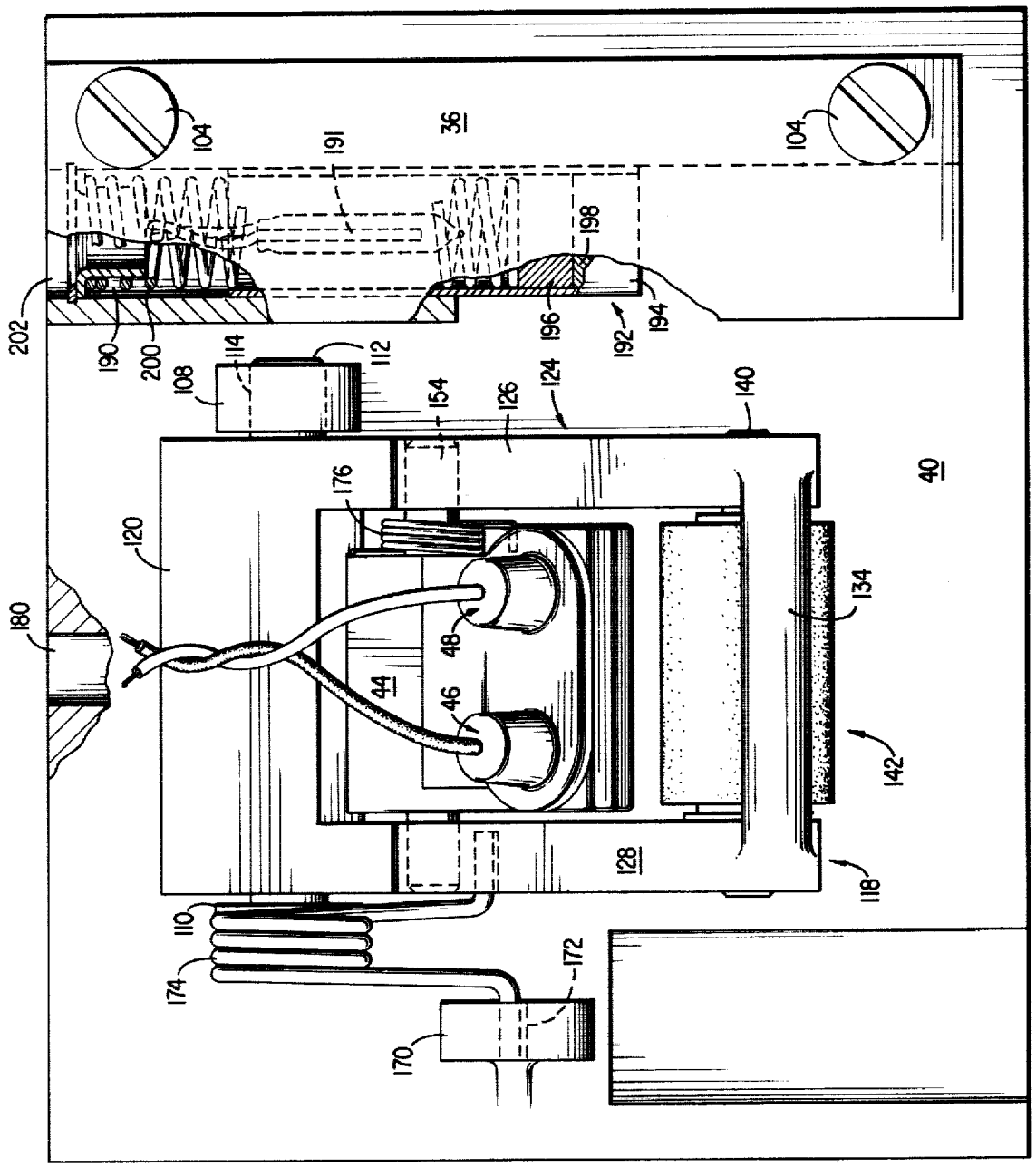
FIG. 13 is a top plan view of the front end mechanism shown in FIG. 8.
Figure 14:
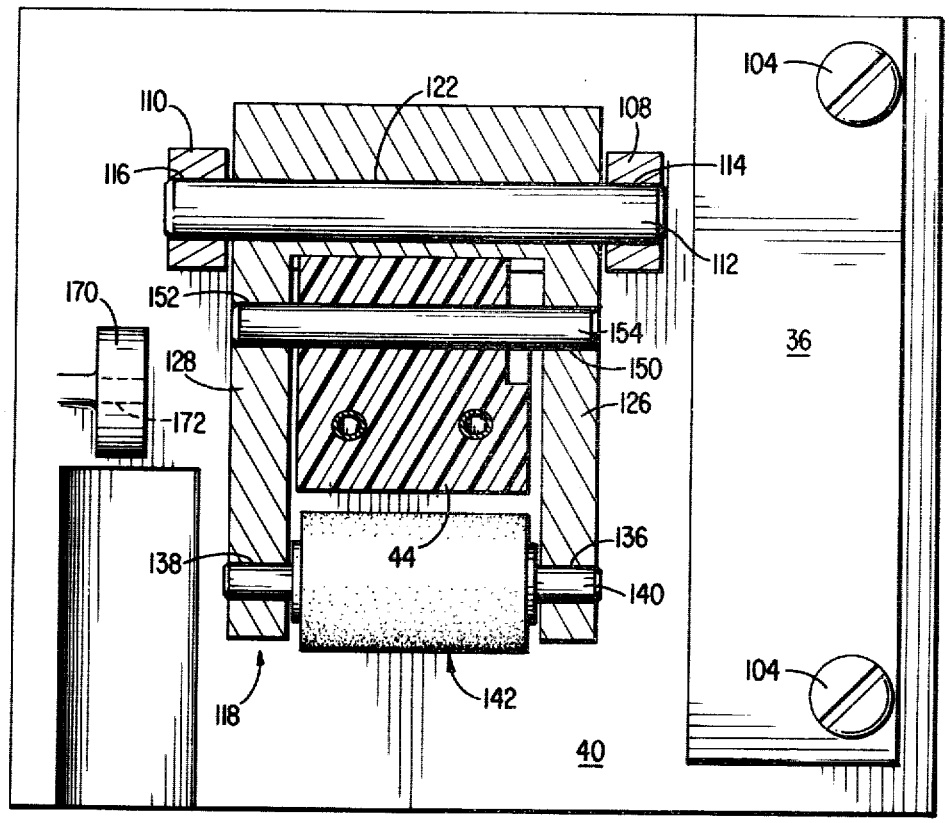
FIg. 14 is a top plan view of the front end mechanism shown in FIG. 8 and partially cut away to reveal the various pivot pins and their mountings.
Figure 15:
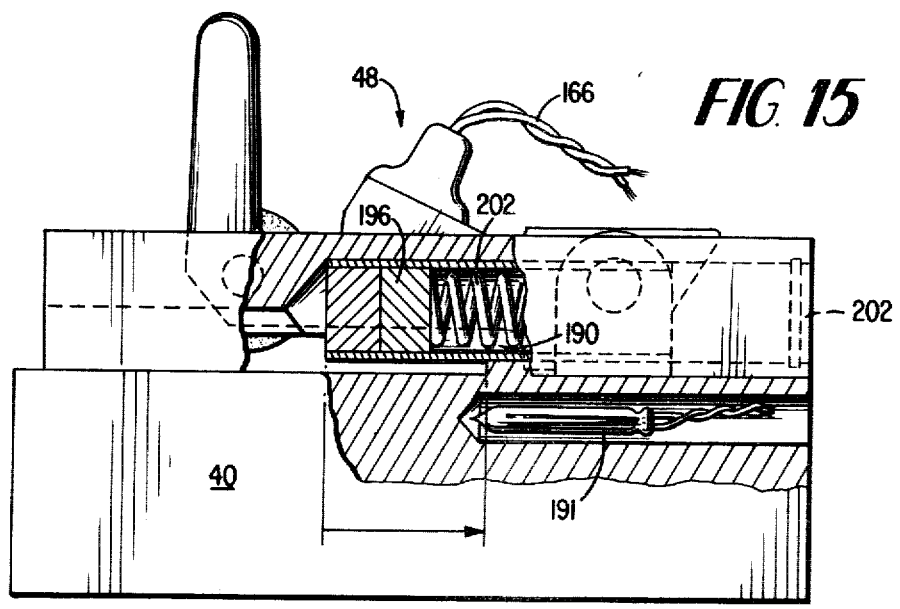
FIG. 15 is a side view partially cut away of the front end mechanism shown in FIG. 8.

As best seen in FIGS. 8, 13 and 14, positioned near the rear of the top surface in a spaced relationship are a pair of uprights 108 and 110. A pivot pin 112 is fixed within apertures 114 and 116 contained in the uprights 108 and 110, respectively, and provides a pivotal axis which is generally at a right angle to the guide groove 106 in the indexing member 36. A yoke 118 is pivotally mounted to the pivot pin 112. The yoke 118 comprises a body portion 120 with a longitudinal bore 122 for receiving the pivot pin 112 and a transversely extending yoke structure generally designated as 124. The yoke structure 124 comprises a pair of transversely extending arms 126 and 128 which radiate from the body portion 120 in a direction toward the front of the instrument 10. Each of the arms terminates in a right angle upright 130 and 132. A cross bar 134 joins the uprights together.

In the yoke 118 where each upright 130, 132 meets an associated arm 126, 128, a bore 136, 138 is provided for receiving a pivot pin 140. As before, the pivot pin defines an axis which is substantially perpendicular to the groove 106 in the indexing member 36.

A resilient roller 142 comprising an outer tubing 144 and a hub 146 is rotatably mounted on the pivot pin 140. The tubing 144 is preferably made of a material which is resilient. One such material is amber latex. The hub 146, on the other hand, is typically made of nylon.

Each of the arms 126, 128 contains a bore 150, 152 which is positioned a short distance ahead of where the arm eminates from the body portion 120. A pivot pin 154 is fixed within the bores 150 and 152 so that the axis of rotation defined by the pivot pin is approximately perpendicular to the groove 106 in the indexing member 36. Pivotally mounted to the pivot pin is a generally L-shaped contact block 44 which is typically molded from Delrin. Positioned within the contact block are a pair of electrical contact assemblies 46 and 48 which are positioned in the block so that both of them will make contact with each of the disc pads 28 and 30, when the sample card is operatively inserted into the front end mechanism 34.

Figure 11:
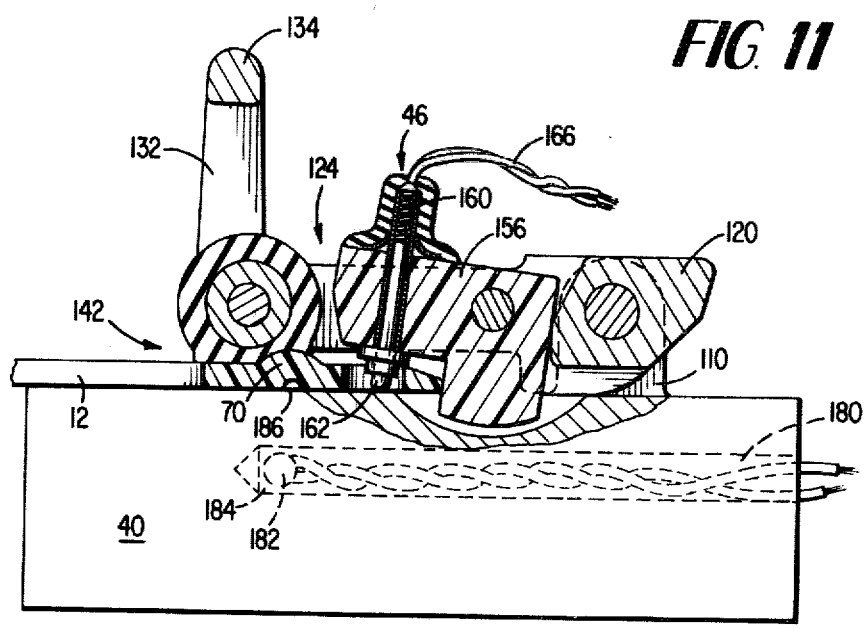

With reference to FIG. 11, each contact assembly is a conventional spring loaded contact mechanism. Using contact assembly 46 as exemplery, a compression spring 160 constantly urges the contact point 162 out of the assembly. In this way, a reliable contact is obtained between the contact point 162 and the steel pad 28 when the sample card is inserted into the instrument.

A connection point 164 for the contact assembly 46 is provided on the opposite side of the contact block 44 away from the contact point 162. An electrical wire 166 is attached to the connection point, and the contact assembly in this area is covered with a molded boot 168 which is typically made of sylastic.

Figure 16A:
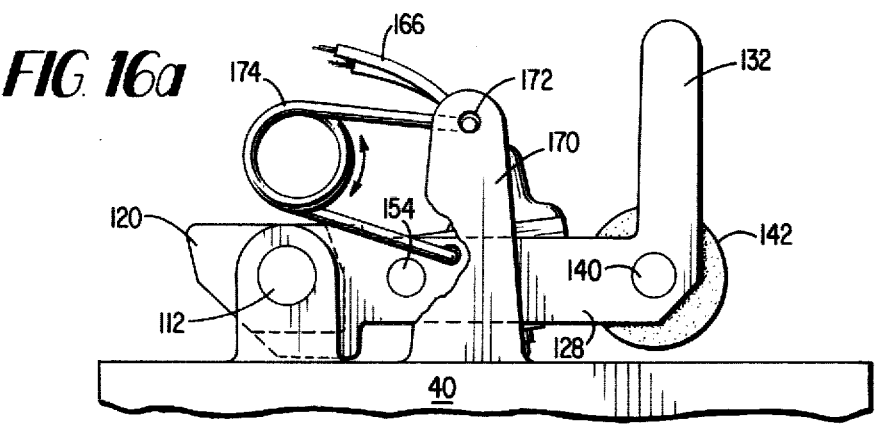
FIG. 16a, 16b and 17 are partial side views showing the yoke and roller assembly of the front end mechanism shown in FIG. 8.

With reference to FIGS. 13 and 16a, spaced from and slightly ahead of upright 110 is a stanchion 170 which contains an aperture 172 for receiving one end of a torsion spring 174. The other end of the torsion spring 174 is secured to the arm 128 of the yoke 118. This spring 174 acts to urge the yoke 118, and thus the resilient member 142, against the top surface 100 of the reference block 40. A second torsion spring 176 (FIG. 17) is positioned on the pivot 154 and has one leg pressing against the underside of the contact block 44 and the other leg pressing against the top surface 100 of reference block 40. This torsion spring 176 acts to constantly urge the contact assemblies 46 and 48 of the contact block 44 away from the top surface 100 of the reference block 40.

As best seen in FIGS. 13 and 11, a bore 180 is provided in the reference block for receiving a thermistor 182 which is potted in place within the bore. The termination area 184 of the bore 180 is chosen so that the thermistor is located relatively close to the portion of the top surface 100 where the blood sample will be located when the sample card is inserted. This general area is denoted as 186 in FIG. 11.

With continued reference to FIGS. 13 and 16, the indexing member 36 contains an elongated cavity 190 which extends from the rear of the indexing member to well within the indexing groove 106. Positioned within the cavity is a member 192 that has a shape which closely resembles the cross-section of the cavity 190 so that the member 192 may be slidably mounted within the cavity. In a preferred embodiment, the member 192 has a cylindrical shape which mates with the generally cylindrical shape of the cavity.

The cylindrical member 192 typically comprises a tube or shell 194 within which is secured a permanent magnet 196. The permanent magnet is preferably a samarium cobalt magnet which is potted within the tube through the use of a suitable epoxy 198. The cylinderical member 192 is positioned within the cavity 190 so that is presents itself within the groove 106 of the indexing member 36. Positioned behind the magnet within the cavity is a compression spring 200 which constantly urges the magnet member 192 forward. The magnet member 192 and spring 200 are held within the cavity by a suitable cap 202 closing the rearward portion of the cavity.

Having discussed the structural details of the sample card 12 and the front end mechanism 34, a discussion of how they interrelate with each other to accomplish proper presentation of a blood sample to the instrument 10 for subsequent hematocrit measurement will now be discussed.

The disposable blood sample card 12 and the instrument 10 constitute the present system for measuring hematocrit. In essence, the blood sample carrier 12 is a micro-volume (typically 0.02 cc) conductivity cell. It is a precision molded plastic part with built-in stainless steel alloy electrodes 22 and 24. The blood sample card assures isolation of the blood sample from either the operator or the instrument. Among the advantages of the blood sample card are that it is used directly as supplied from the manufacturer, pre-conditioning is not required, and, after its one-time use, it is discarded leaving no post-measurement clean-up.

The blood sample contained in the capillary tube 18 of the sample card 12 is used directly as it comes from the patient with no pre-dilution or anti-coagulant additive steps. The disposable blood sample card is loaded with a blood sample in the following manner. In the case of a patient, the area, such as the finger or earlobe, where the blood sample is to be drawn, is first cleaned with isopropyl alcohol. The area is then allowed to dry after which it is punctured with a lancet. The first drop of blood is wiped away with a clean gauze. Without squeezing the sample area, the nozzle 20 of the sample card is placed against the puncture site, and the blood sample is drawn into the capillary tube 18 by capillary action. Blood should fill the capillary tube 18 such that it covers both electrodes 22 and 24 and the volume 26 between them. The blood sample must be free of air bubbles, foam, clots, etc. It may sometimes be necessary to tap the disposable sample card to enhance capillary action.

In the case of a laboratory sample, the blood sample is mixed gently with an anti-coagulant which is added when the original veni-puncture is taken. It is not necessary to add additional anti-coagulant. The nozzle 20 of the sample card 12 is placed near the laboratory blood sample, and, as before, the blood sample is drawn into the capillary tube 18 by capillary action.

In loading the sample card with the blood sample, certain advantageous aspects of the card are noted. The blood sample carrier is translucent so that the user can hold the blood sample carrier up to the light, look through it, and ensure that there are no discontinuities in the blood sample. The capillary section 70 provides a magnifying area so that any small air pockets or discontinuities in the blood sample are more readily apparent.

In order to make an accurate hematocrit measurement, it is necessary to know two things about the blood: blood conductivity and temperature. As is readily apparent, the volume 26 within the capillary tube 18 of the sample card, is so small that it would be very difficult to obtain the temperature of the blood sample directly. Therefore, an alternative approach is presented in the present invention.

When a reading is to be taken, the blood sample card is pressed into intimate contact with top surface 100 of the reference block 40 of the front end mechanism 34 which forms part of the instrument 10. The reference block 40 is made of a material which has excellent heat conducting characteristics. One such material is aluminum. Thus, with the blood sample card pressed against the block, the temperature of the blood is forced to the temperature of the block. The thermistor 182 imbeded in the block thus gives an accurate reading of the temperature of the blood.

In inserting the disposable sample card within the instrument to obtain a hematocrit reading, the blood sample card is oriented with respect to the entrance 94 of the instrument 10 so that the arrow 92 on the card points to the entrance of the instrument and the bump 70 in the capillary tube 18 is uppermost. The sample card is then inserted within the front end mechanism 34 of the instrument so that the wing 64 of the card rides in the groove 106 of the indexing member 36 (FIG. 8).

As the sample card rides in the groove 106 of the indexing member and along the top surface 100 of the block 40, the bump 70 in the capillary tube interfaces with the roller 142 (FIG. 10). As soon as the bump 70 passes under the roller 142, the torsion spring 174 urges the roller against the top surface 56 of the blood sample card and holds the bottom surface 74 of the card in intimate contact with the top surface 100 of the block 40 (FIG. 11).

The forward end 60 of the sample card 12 pushes against the L-shaped bracket 156 (FIG. 10), and the two contact assemblies 46 and 48 are forced down into the holes 80 and 82 in the sample card to make electrical contact with the pads 28 and 30 which are associated with the two electrodes 22 and 24 (FIG. 11). Because the contact assemblies are spring loaded, a reliable contact between the contact points 162 of the assemblies 46, 48 and the pads 28, 30 is ensured.

After a reading has been obtained, the sample card is removed and the L-shaped bracket 156 moves into its original position. The capillary tube bump 70 of the sample card 12 again bumps under the roller 142 and, after passing under the roller, the sample card may be freely removed.

Figure 12:
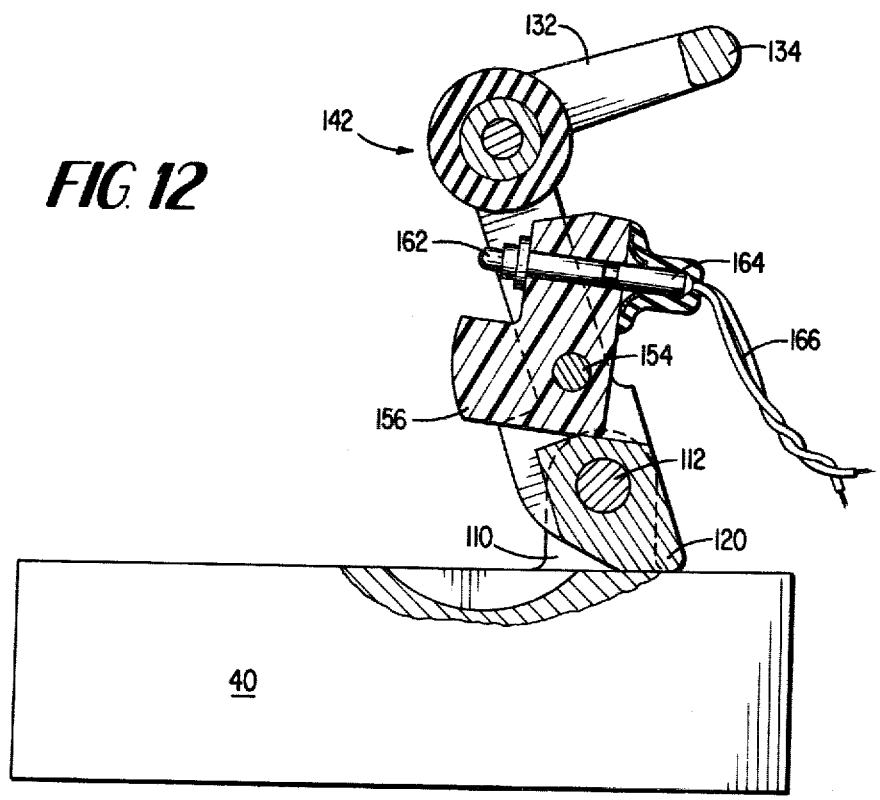
Figure 16B:
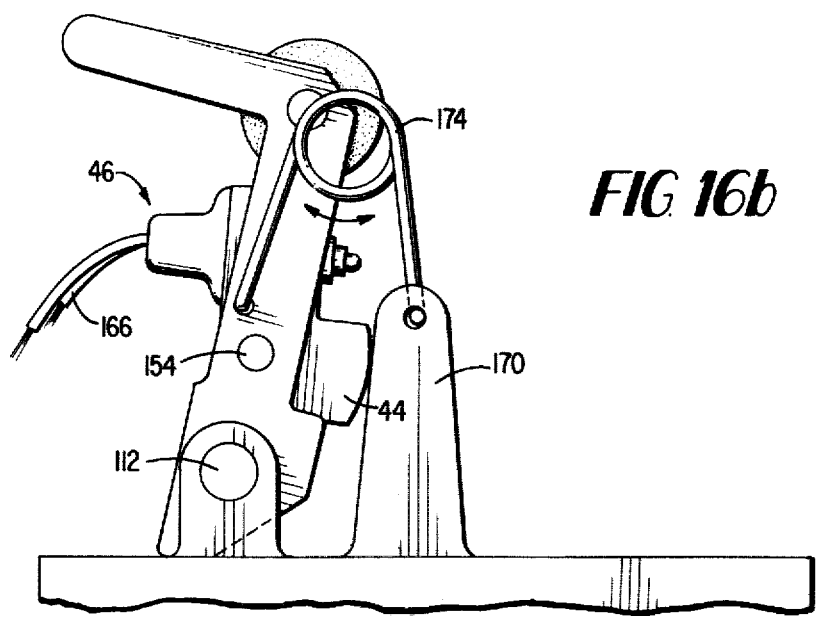
Figure 17:
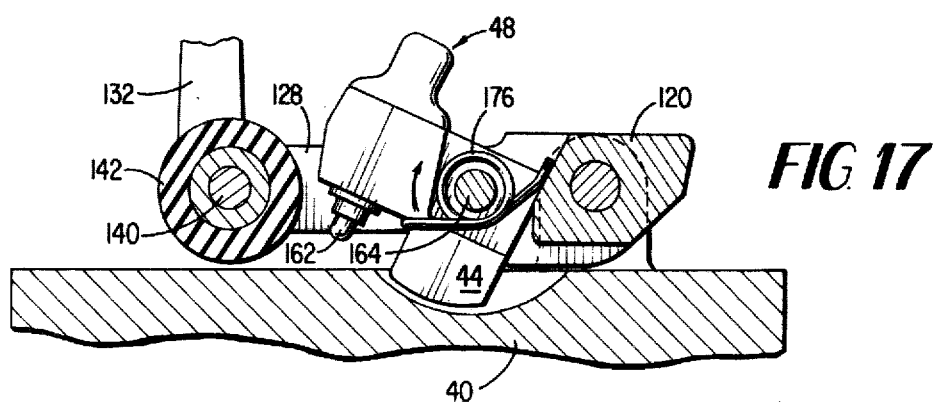

One advantageous feature of the instrument 10, is the ease with which the contact assemblies 46 and 48 may be cleaned. The instrument 10 contains a cover 220 which may be flipped up to reveal the yoke 118 and roller assembly 42. An operator may grasp the cross piece 134 of the yoke and draw the assembly 42 out of the top cover, as shown in FIGS. 12 and 16b. This presents the contact assemblies 46, 48 and the surrounding areas in an easy to clean attitude so that the whole block area where blood might have congealed and formed can be cleaned.

The instrument also has carrying handle 260 and a storage compartment 262 for storing the pre-packaged disposable sample cards.

Although the present invention has been shown and described in terms of a preferred embodiment, it will be appreciated by those skilled in the art, that changes or modifications are possible which do not depart from the inventive concepts described and taught herein. Such changes and modifications are deemed to fall within the purview of these inventive concepts.

What is claimed is:

1. A sample card for use in electrically operating on a liquid sample, the card comprising:
   a body portion;
   a capillary tube defined in said body portion for receiving a liquid sample;
   first and second electrode means disposed within said capillary tube in a spaced relationship;
   measurement cell means formed by said capillary tube and bounded by said first and second electrode means for housing a predetermined volume of said liquid sample; and
   means adapted to operatively associate said first and second electrode means with an electrical signal.

2. The sample card of claim 1 further comprising entrance means for providing an entrance for said liquid sample into said capillary tube.

3. The sample card of claim 1, wherein said entrance means is a nozzle.

4. The saple card of claim 1, further comprising magnifying means for allowing a user to view an enlarged image of said measurement cell.

5. The sample card of claim 1, further comprising vent means for venting air in said capillary tube as said liquid sample is drawn into said tube by capillary action.

6. The sample card of claim 1, further comprising an evacuated portion in said body portion near said capillary tube.

7. The sample card of claim 1, further comprising guide means on said body portion, said guide means adapted to ensure proper orientation when said sample card is inserted in a device which electrically operates on said liquid sample.

8. The sample card of claim 1, further comprising registering means on said body portion, said registering means adapted to ensure proper registration when said sample card is positioned in a device which electrically operates on said liquid sample.

9. A blood sample carrier for use in measuring conductivity of a blood sample, said carrier comprising:
   capillary tube means for receiving a blood sample;
   first and second electrode means disposed within said capillary tube means in a spaced relationship;
   measurement cell means, formed by said capillary tube means and bounded by said first and second electrode means, for segregating a predetermined volume of said liquid sample; and
   means adapted to operatively associate said first and second electrode means with an electronic conductivity measuring circuit.

10. The blood sample carrier of claim 9, further comprising entrance means for providing an entrance for said liquid sample into said capillary tube means.

11. The blood sample carrier of claim 9, wherein said entrance means is a nozzle.

12. The sample card of claim 9, further comprising magnifying means for allowing a user to view an enlarged image of said measurement cell.

13. The sample card of claim 9, further comprising an evacuated portion in said body portion near said capillary tube means.

14. The sample card of claim 9, further comprising guide means on said body portion, said guide means adapted to ensure proper orientation when said sample card is inserted in a device which electrically operates on said liquid sample.

15. The sample card of claim 9, further comprising registering means on said body portion, said registering means adapted to ensure proper registration when said sample card is positioned in a device which electrically operates on said liquid sample.

16. A blood sample carrier for use in electrically measuring a parameter of a blood sample, said carrier comprising:
   a planar base portion;
   a hollow tube having an interior surface that defines a capillary tube on said base;
   first and second electrodes disposed on a portion of said interior surface in a spaced relationship;
   a measurement cell defined by said interior surface and said first and second electrodes, said measurement cell segregating a predetermined volume of said blood sample being measured; and
   pad means, on said base, adpatd for electrically associating said first and second electrodes with a blood parameter measuring device.

17. The sample carrier of claim 16, wherein said interior surface of said capillary tube, when viewed in cross-section, is in the shape of a semicircle.

18. The sample carrier of claim 17, wherein said first electrode is disposed along the flat portion of a first cross-sectional semicircle and said second electrode is disposed along the flat portion of a second cross-sectional semicircle, said first and second semicircles being substantially parallel to and spaced from each other.

19. The sample carrier of claim 16, wherein said pad means comprises a first electrically conductive disc positioned on said base and connected to said first electrode, and a second electrically conductive disc positioned on said base and connected to said second electrode.

20. The sample card of claim 16, further comprising vent means for venting air in said capillary tube as said liquid sample is drawn into said tube by capillary action.

21. The sample card of claim 16, further comprising an evacuated portion in said body portion near said capillary tube.

22. The sample card of claim 16, further comprising guide means on said body portion, said guide means adapted to ensure proper orientation when said sample card is inserted in a device which electrically operates on said liquid sample.

23. The sample card of claim 16, further comprising registering means on said body portion, said registering means adapted to ensure proper registration when said sample card is positioned in a device which electrically operates on said liquid sample.

24. A method of making a disposable liquid sample carrier comprising the steps of:
forming a portion of a base member into a portion of the interior surface of a capillary tube;
providing an overlay having a surface;
positioning and securing two electrodes in a spaced relationship on said surface of said overlay; and
positioning and securing said overlay to said base member so that said surface of said overlay completes the interior surface of said capillary tube and so that said two electrodes along with the interior surface of said capillary tube segregates a volume constituting a measurement cell.

25. The method of claim 24, further comprising the step of configuring said interior surface of said capillary tube so that its transverse section resembles a semicircle.

26. The method of claim 25, wherein said providing step comprises providing an overlay having a substantially planar surface.

27. The method of claim 24, further comprising the step of forming a nozzle at an end of said capillary tube.

28. The method of claim 27, wherein said nozzle forming step includes forming a portion of the interior surface of said nozzle from said base member and the remainder of the interior surface of said nozzle from said overlay.

29. The method of claim 24, further comprising the step of making said base member from a translucent material.

30. The method of claim 29, wherein said translucent material is selected from the group consisting of polycarbonate, polymethacrylate, and styrene-butadiene resin.

31. The method of claim 24, further comprising the step of making said overlay from a translucent material.

32. The method of claim 24, further comprising the step of making said overlay from a Mylar.

33. The method of claim 24, further comprising the step of making said electrodes of stainless steel alloy.

34. The method of claim 24, wherein said electrode positioning and securing step includes securing a stainless steel alloy sheet to said overlay and etching away all of said stainless steel sheet except the portion defining said electrodes.

35. The method of claim 34, wherein said etching step is a photoetching step.

36. The method of claim 24, wherein said overlay is secured to said base member by employing an adhesive.

37. The method of claim 24, wherein said electrodes are secured to said overlay by employing an adhesive.

38. The method of claim 24, further comprising the step of forming a guide member on said base member.

* * * * *